(12) United States Patent
Missling

(10) Patent No.: US 11,622,955 B2
(45) Date of Patent: Apr. 11, 2023

(54) SIGMA-1 RECEPTOR AGONIST SYSTOLIC BLOOD PRESSURE THERAPY

(71) Applicant: ANAVEX LIFE SCIENCES CORP., New York, NY (US)

(72) Inventor: Christopher U. Missling, New York, NY (US)

(73) Assignee: ANAVEX LIFE SCIENCES CORP., New York, NY (US)

( * ) Notice: Subject to any disclaimer, the term of this patent is extended or adjusted under 35 U.S.C. 154(b) by 222 days.

(21) Appl. No.: 16/767,990

(22) PCT Filed: Nov. 28, 2018

(86) PCT No.: PCT/US2018/062853
§ 371 (c)(1),
(2) Date: May 28, 2020

(87) PCT Pub. No.: WO2019/108653
PCT Pub. Date: Jun. 6, 2019

(65) Prior Publication Data
US 2021/0186920 A1    Jun. 24, 2021

Related U.S. Application Data

(60) Provisional application No. 62/591,248, filed on Nov. 28, 2017.

(51) Int. Cl.
A61K 31/341    (2006.01)
A61K 9/00      (2006.01)
A61K 45/06     (2006.01)

(52) U.S. Cl.
CPC .......... *A61K 31/341* (2013.01); *A61K 9/0019* (2013.01); *A61K 9/0053* (2013.01); *A61K 45/06* (2013.01)

(58) Field of Classification Search
CPC .................................................... A61K 31/341
See application file for complete search history.

(56) References Cited

U.S. PATENT DOCUMENTS

| 2007/0196510 A1 | 8/2007 | Gerber et al. |
| 2014/0170157 A1 | 6/2014 | Agarwal et al. |
| 2021/0085637 A1* | 3/2021 | Missling .............. A61K 9/0053 |

FOREIGN PATENT DOCUMENTS

WO    2018022848 A1    2/2018

OTHER PUBLICATIONS

Grimm et al. CAS: 134: 247078, 2001.*
Jalil et al. CAS: 131:27722, 1999.*
International Search Report and Written Opinion dated Jan. 31, 2019 in corresponding International Patent Application No. PCT/US2018/062853.

* cited by examiner

*Primary Examiner* — Rei Tsang Shiao
(74) *Attorney, Agent, or Firm* — Polsinelli PC

(57) ABSTRACT

A method for lowering systolic blood pressure in a patient exhibiting resistance to a antihypertensive therapy with one or more drugs, the method comprising administering to the patient ANAVEX®2-73 at a dose and frequency effective to provide a reduction of at least about 3 mmHg in one or more blood pressure parameters selected from trough sitting systolic, 24-hour ambulatory systolic, and maximum diurnal systolic blood pressures.

22 Claims, 1 Drawing Sheet

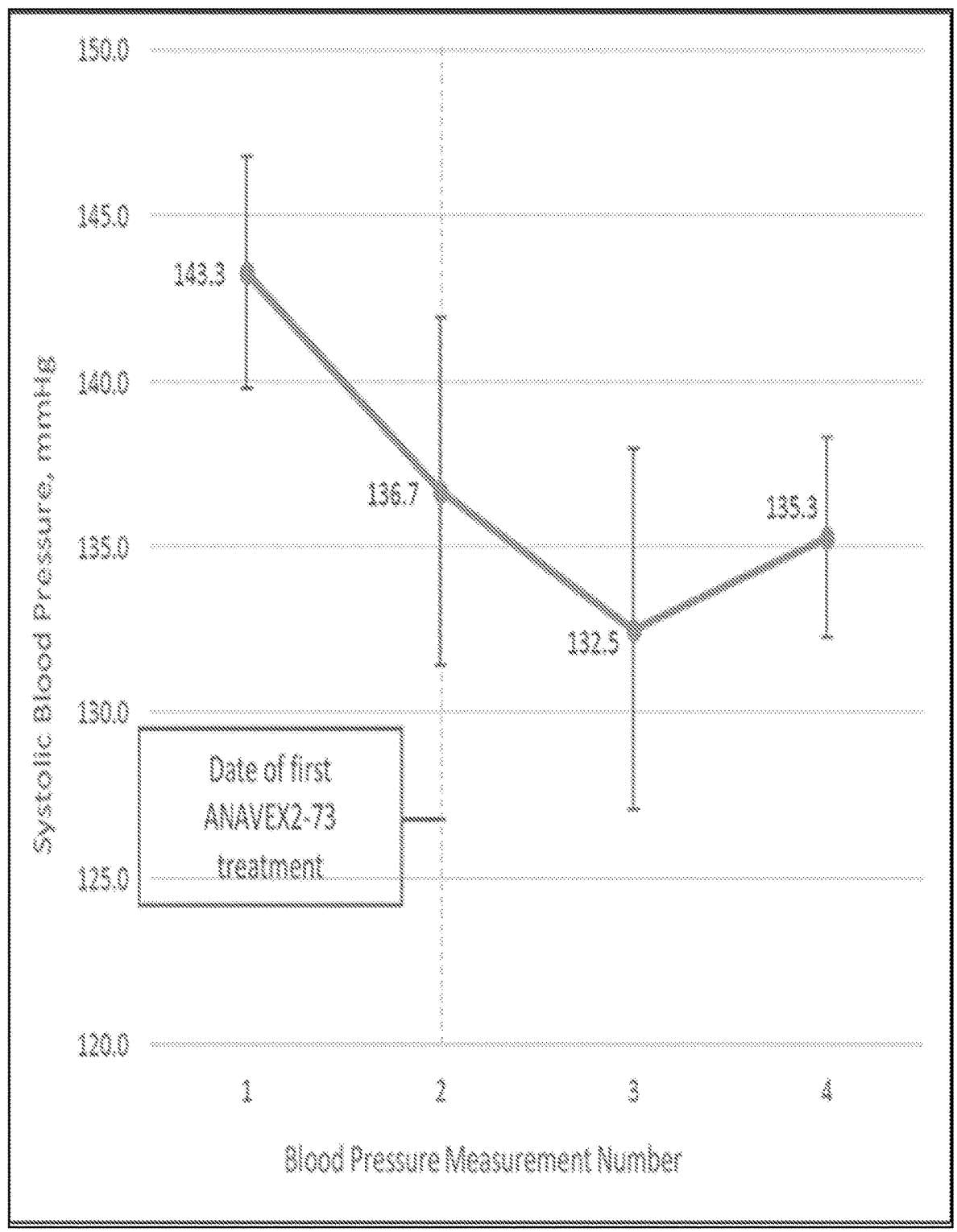

SIGMA-1 RECEPTOR AGONIST SYSTOLIC BLOOD PRESSURE THERAPY

CROSS REFERENCE TO RELATED APPLICATIONS

This application is a national stage filing under 35 U.S.C. § 371 of International Application No. PCT/US2018/062853, filed Nov. 28, 2018, which claims the benefit of U.S. provisional application No. 62/591,248, filed on Nov. 28, 2017, the disclosure of each is hereby incorporated by reference in its entirety.

FIELD OF THE INVENTION

The present disclosure generally relates to methods for lowering systolic blood pressure in a patient exhibiting resistance to an antihypertensive therapy with one or more drugs, the methods comprising administering to the patient a therapeutically effective amount of tetrahydro-N,N-dimethyl-2,2-diphenyl-3-furanmethanamine hydrochloride.

BACKGROUND OF THE INVENTION

The sigma-1 (σ-1) receptor is a calcium-sensitive endoplasmic reticulum chaperone protein associated with maintaining cellular calcium levels and proper protein folding. This receptor is believed important in conserving cellular homeostasis in the presence of cellular stress and inflammation. Several studies demonstrate that sigma-1 receptor stimulation promotes neuroprotection, neuroplasticity, cardioprotection, and renoprotection.

ANAVEX®2-73 (hereinafter "A2-73"), tetrahydro-N,N-dimethyl-2,2-diphenyl-3-furanmethanamine hydrochloride, is a combined sigma-1 receptor agonist with reported muscarinic (M1-M4) receptor activity. A2-73 was studied in both Phase I and Phase IIa clinical trials as a therapeutic for treatment of Alzheimer's disease and found to be well tolerated by human patients. In rats, reportedly sigma-1 receptor stimulation promotes endothelial and neuronal nitric oxide synthase activation and nitric oxide production, resulting in vasodilation and potentially mediating blood pressure (BP) decline. It has been reported that M3 receptor stimulation triggers nitric oxide-mediated central vasodilation. One report finds that an M3 antagonist reduces blood pressure. (Kario et al., "Sleep-predominant lowering of ambulatory blood pressure by bedtime inhalation of a novel muscarinic M3 receptor antagonist: a new 'bronchoantihypertensive' strategy targeting the lung in hypertension with chronic obstructive pulmonary disease", HYPERTENS RES. 2008 April: 31(4):817-21. doi: 10.1291/hypres.31.817). Medication-induced stimulation of this receptor may further contribute to blood pressure (BP) modification in a given subject. Historically, clinical trials and clinical practice placed greater importance on diastolic blood pressure (DBP) levels. Older reports defined DBP as the basis for detection and treatment with blood pressure of 180/85 mmHg as ineligible for treatment under then-existing guidelines. Systolic hypertension, often thought to be a result of hardening and loss of elasticity of the major arteries, was viewed as an unavoidable consequence of aging. DBP was often viewed as a function of peripheral resistance. SBP generally continues to rise with advancing age while DBP stabilizes or declines. The end result is termed isolated systolic hypertension (ISH), which is generally understood to mean a systolic blood pressure of greater than 140 mm Hg.

Treatment of ISH with thiazine diuretics and calcium antagonists or calcium channel blockers has been reported. Reference is made to therapeutic treatment with chlorothalidone (and optionally including atenolol or reserpine), nitrendipine, nifedipine, eprosartan, and hydrochlorothiazide. In addition, ACE inhibitors, AT1-blockers, spironolactone and omapatrilate are candidate therapeutics.

SUMMARY OF THE INVENTION

This present disclosure provides a method of treating isolated systolic hypertension, which comprises administering to a subject in need thereof an effective amount of A2-73. It further includes use of A2-73 in the manufacture of a medicament for the treatment of isolated systolic hypertension.

Additionally included in the disclosure is a pharmaceutical composition for use in the treatment of isolated systolic hypertension which comprises A2-73 and a pharmaceutically acceptable carrier. The pharmaceutical composition comprising A2-73 may be formulated to be administered orally or by intravenous injection as appropriate.

Further included in the disclosure is a method for lowering systolic blood pressure in a subject in need thereof, the method comprising administering to the patient A2-73 at a dose and frequency effective to provide a reduction of at least about 3 mmHg in one or more blood pressure parameters selected from trough sitting systolic, 24-hour ambulatory systolic, and maximum diurnal systolic blood pressures, wherein the subject exhibits resistance to antihypertensive therapy with one or more antihypertensive drugs that are not A2-73.

Any of the methods disclosed herein for lowering systolic blood pressure may involve administering a combination of A2-73 and another one or more anti-hypertensive drugs, such drugs selected from beta blockers, thiazide diuretics, ACE inhibitors, and calcium channel blockers. The combination may comprise simultaneous or separate schedules of administration for each of the drugs administered.

Therapeutically effective doses of A2-73 are from about 1 mg to about 60 mg. In some aspects the therapeutically effective dose is about 30 mg to about 50 mg, particularly for oral administration. In other aspects, the therapeutically effective dose is about 3 mg to about 5 mg, particularly for intravenous administration. The present disclosure contemplates that a therapeutically effective dose may be administered at least once daily. In other aspects A2-73 is administered according to an intermittent dosing regimen of at least two cycles, each cycle comprising (a) a dosing period during which a therapeutically effective dose of said pharmaceutical composition is administered to said patient and, thereafter, (b) a resting period. In some aspects the dosing period and the resting period are of the same duration or are of different durations. In some aspects, the dosing period and alternating resting period are in the range of a lower limit of about 1 day, 2 days, 3 days, 4 days, 5 days, 6 days, 7 days, 8 days, 9 days, 10 days, 11 days, 12 days, 13 days, and 14 days to an upper limit of about 28 days, 27 days, 26 days, 25 days, 24 days, 23 days, 22 days, 21 days, 20 days, 19, days, 18 days, 17 days, 16 days, 15 days, and 14 days.

DESCRIPTION OF THE DRAWINGS

FIG. 1 is a graph of systolic blood pressure readings of 32 human patients of both sexes, across multiple visits, adjusted for time of BP measurement, gender, age, body mass index, and previous or concurrent use of antihypertensive medication.

DETAILED DESCRIPTION OF THE INVENTION

Various aspects of the present disclosure are discussed in detail below. While specific implementations are discussed, it should be understood that this is done for illustration purposes only. A person skilled in the relevant art will recognize that other components and configurations may be used without parting from the spirit and scope of the disclosure.

It should be understood at the outset that although illustrative implementations of one or more aspects are illustrated below, the disclosed method may be implemented using any number of techniques. The disclosure should in no way be limited to the illustrative implementations, drawings, and techniques illustrated herein, but may be modified within the scope of the appended claims along with their full scope of equivalents.

In the following discussion and in the claims, the terms "including" and "comprising" are used in an open-ended fashion, and thus should be interpreted to mean "including, but not limited to . . . ". The various characteristics described in more detail below, will be readily apparent to those skilled in the art with the aid of this disclosure upon reading the following detailed description, and by referring to the accompanying drawings.

According to one aspect of the present disclosure, A2-73 can be produced by charging a solution of tetrahydro-N,N-dimethyl-2,2-diphenyl-3-furanmethanamine free base in ethyl acetate with isopropanol. The ethylacetate is removed by distillation and the remaining isopropanol solution containing tetrahydro-N,N-dimethyl-2,2-diphenyl-3-furanmethanamine free base is clear filtered. Aqueous hydrochloric acid (1.1 eq) is charged to the isopropanol solution and the formed crystalline HCl salt of tetrahydro-N,N-dimethyl-2,2-diphenyl-3-furanmethanamine, (A2-73), is isolated by filtration and dried under vacuum at 55° C. for 3 days.

The safety of A2-73 has been demonstrated in a randomized, placebo-controlled single ascending dose Phase 1 study of A2-73 in 22 healthy male volunteers. (See Ole Voges, Ingo Weigmann, Norman Bitterlich, Christoph Schindler and Christopher Missling, "A Phase 1 Dose Escalation Study to Investigate Safety, Tolerability, and Pharmacokinetics of ANAVEX2-73 in Healthy Male Subjects," CNS Summit 2014, Boca Raton, Fla., the entire disclosure of which is herein incorporated by reference). Ascending single oral doses of 1 mg, 10 mg, 30 mg, 40 mg, 50 mg, and 55 mg of A2-73 were safe and well tolerated in healthy subjects. No serious adverse events occurred. Based on the frequency and intensity of non-treatment emergent adverse events the maximum tolerable dose and the minimum intolerable dose were defined as 55 mg and 60 mg, respectively. At the highest doses, observed adverse events included moderate and reversible dizziness and headache, common in drugs that target the central nervous system. Blood pressure and resting heart rate and other clinical parameters such as vital signs and 12-lead electrocardiogram (ECG) did not show any clinically relevant or dose-dependent changes. The pharmacokinetics of A2-73 was found to be suitable for daily oral dosing.

The present disclosure generally relates to pharmaceutical compounds and compositions for the treatment of high systolic blood pressure (SBP). More particularly, the present disclosure relates to the use of pharmaceutical compositions containing A2-73 for the treatment of high SBP.

SBP is therapeutically lowered by a method as described herein. Blood pressure is determined by any of a variety of methods known in the art, including by sphygmomanometry. Blood pressure is typically measured in a sitting or ambulatory subject.

Another measure of blood pressure is "24-hour ambulatory" blood pressure. A "24-hour ambulatory" systolic or diastolic BP is an average of systolic or diastolic measurements taken repeatedly in the course of a 24-hour period, in an ambulatory subject.

"Maximum diurnal" systolic or diastolic BP is a measure of highest systolic or diastolic blood pressure recorded in a 24-hour period. Without being bound by any particular theory, it is believed that a maximal diurnal BP reflects the peak of the natural diurnal blood pressure cycle, typically occurring in the morning, for example between about 5 am and about 11 am. Commonly, a second peak occurs in the evening, for example between about 5 pm and 10 pm. Such a bimodal waveform diurnal ambulatory BP pattern may be especially characteristic of resistant hypertension.

A common feature of resistant hypertension is a nighttime (defined herein as 2200 to 0600) mean systolic ambulatory BP that is less than about 10% lower than the daytime (defined herein as 0600 to 2200) mean systolic ambulatory BP. The parameter herein termed "day/night ambulatory BP ratio" expressed as a percentage is calculated as (daytime mean-nighttime mean)/daytime mean ×100. A diurnal ambulatory BP (ABP) pattern having a day/night ABP ratio of less than about 10% is sometimes referred to as a "non-dipping ABP."

As disclosed herein, a subject patient receiving A2-73 who exhibits therapeutic systolic blood pressure lowering according to a method of the invention is, in some aspects, a subject exhibiting resistance to antihypertensive therapy with one or more drugs other than A2-73.

It has now been found in a clinical study of post-hoc evaluation of unexpected declines in systolic blood pressure (SBP) that were observed in a phase IIa clinical trial for treatment of Alzheimer's disease using A2-73. BPs were measured at four time points during the study period: 1) the day of screening for enrollment, 2) day one of treatment with either oral or intravenous medication (BP measurements were obtained prior to medication administration), 3) day 25 of treatment (when patients crossed over to receive whichever formulation, oral or intravenous, they had not received previously), and 4) day 36 (conclusion of the PART A of the Phase IIa study). Statistical analyses included paired t-testing comparing changes in BPs across each measurement, as well as multivariable linear mixed effects modeling (adjusted for time of measurement, gender, age, body mass index, and use of antihypertensive medication) to account for within-individual repeated measurements over time.

Thirty-two Alzheimer's disease patients took part in the phase IIa trial. Mean age was 69.5 (standard deviation [SD] 9.8) years, 60% were male, mean body mass index was 26.5 (SD 3.9) kg/m2, and 50% were on antihypertensive medication at the time of screening. In unadjusted analyses, there was a significant decline in SBP comparing the first measurement (mean SBP 143.3, SD 19.7, mmHg) to all subsequent measurements (p=0.007, 0.001, and 0.007, respectively). There was a mean 8.7 (SD 3.0) mmHg SBP decline between the first and second measurements (i.e., immediately prior to the first treatment), but no significant decline comparing the second measurement to all subsequent measurements (p=0.120 and 0.972, respectively). In multivariable adjusted models (FIG. 1), there was no significant difference in SBP between the first and second readings (p=0.211). There was, however, a significant decline in SBP between the first reading and the other subsequent readings (p=0.048 and 0.008, respectively), as shown in FIG. 1. Of note, no patients reported any changes in their antihypertensive regimen while taking part in the trial.

No previous reports were found of a decline in SBP following treatment with a sigma-1 receptor agonist. This class of medications thus provides a novel mechanism for systolic BP reduction useful in treating isolated systolic hypertension. The efficacy of A2-73 is presented graphically in FIG. 1, presenting repeated systolic BP readings across visits, adjusted for time of BP measurement, gender, age, body mass index, and use of antihypertensive medication. The beneficial effect of lowering systolic blood pressure included patients exhibiting resistance to many of the existing classes of anti-hypertensive drugs and thus represents a significant advance is the treatment of high systolic blood pressure.

In some aspects, combination dosages comprising A2-73 and at least one beta blocker, such as propanolol ((RS)-1-(1-methylethylamino)-3-(1-naphthyloxy)propan-2-ol), burcindolol (2-[2-hydroxy-3-[[2-(1H-indol-3-yl)-1,1-dimethyl-ethyl]amino]propoxy]benzonitrile), carteolol ((RS)-5-[3-(tert-butylamino)-2-hydroxypropoxy]-3,4-dihydroquinolin-2(1H)-one), carvedilol ((±)-[3-(9H-carbazol-4-yloxy)-2-hydroxypropyl][2-(2-methoxyphenoxy)ethyl]amine), labetalol ((RS)-2-Hydroxy-5-[1-hydroxy-2-[(4-phenylbutan-2-yl)amino]ethyl]benzamide), nadolol (rel-(2R,3S)-5-{[(2R)-3-(tert-butylamino)-2-hydroxypropyl]oxy}-1,2,3,4-tetrahydronaphthalene-2,3-diol), oxprenolol ((RS)-1-[2-(Allyloxy)phenoxy]-3-(isopropylamino)propan-2-ol), penbutolol ((S)-1-(tert-butylamino)-3-(2-cyclopentylphenoxy)propan-2-ol), pindolol ((RS)-1-(1H-indol-4-yloxy)-3-(isopropylamino)propan-2-ol), sotalol ((RS)—N-{4-[1-hydroxy-2-(propan-2-ylamino)ethyl]phenyl}methanesulfonamide), timolol ((S)-1-(tert-Butylamino)-3-[(4-morpholin-4-yl-1,2,5-thiadiazol-3-yl)oxy]propan-2-ol), acebutolol ((RS)—N-{3-acetyl-4-[2-hydroxy-3-(propan-2-ylamino)propox]phenyl}butanamide), atenolol ((RS)-2-{4-[2-Hydroxy-3-(propan-2-ylamino)propoxy]phenyl}acetamide), betaxolol ((RS)-1-{4-[2-(cyclopropylmethoxy)ethyl]-phenoxy}-3-(isopropylamino)propan-2-ol), bisoprolol ((RS)-1-{4-[(2-isopropoxyethoxy)methyl]phenoxy}-3-(isopropylamino)propan-2-ol), celiprolol ((RS)—N'-{3-Acetyl-4-[3-(tert-butylamino)-2-hydroxypropoxy]phenyl}-N,N-diethylurea), metoprolol ((RS)-1-[4-(2-Methoxyethyl)phenoxy]-3-[(propan-2-yl)amino]propan-2-ol), nebivolol (1RS,1'RS)-1,1'-[(2RS,2'SR)-bis(6-fluoro-3,4-dihydro-2H-1-benzopyran-2-yl)]-2,2'-iminodiethanol or 1-(6-Fluorochroman-2-yl)-{[2-(6-fluorochroman-2-yl)-2-hydroxyethyl]amino}ethanol or 2,2'-Azanediylbis(1-(6-fluorochroman-2-yl)ethanol) or 1-(6-Fluoro-3,4-dihydro-2H-1-benzopyran-2-yl)-2-{[2-(6-fluoro-3,4-dihydro-2H-1-benzopyran-2-yl)-2-hydroxyethyl]amino}ethan-1-ol or combinations thereof), esmolol (methyl (RS)-3-{4-[2-hydroxy-3-(propan-2-ylamino)propoxy]phenyl}propanoate), butaxamine ((1S,2S)-1-(2,5-dimethoxyphenyl)-2-(tert-butylamino)propan-1-ol), ICI-118,551 (3-(isopropylamino)-1-[(7-methyl-4-indanyl)oxy]butan-2-ol), and SR 59230A ((2S)-1-(2-Ethylphenoxy)-3-{[(1S)-1,2,3,4-tetrahydronaphthalen-1-yl]amino}propan-2-ol) are contemplated for reducing SBP.

In other aspects, combination dosages comprising A2-73 and at least one thiazine diuretic, such as chlorthalidone ((RS)-2-Chloro-5-(1-hydroxy-3-oxo-2,3-dihydro-1H-isoindol-1-yl)benzene-1-sulfonamide), hydrochlorothiazide (6-chloro-1,1-dioxo-3,4-dihydro-2H-1,2,4-benzothiadiazine-7-sulfonamide), methyclothiazide (6-Chloro-3-(chloromethyl)-2-methyl-3,4-dihydro-2H-1,2,4-benzothiadiazine-7-sulfonamide 1,1-dioxide), metolazone (7-chloro-2-methyl-4-oxo-3-o-tolyl-1,2,3,4-tetrahydroquinazoline-6-sulfonamide), indapamide (4-chloro-N-(2-methyl-2,3-dihydroindol-1-yl)-3-sulfamoyl-benzamide), bendroflumethiazide (3-Benzyl-1,1-dioxo-6-(trifluoromethyl)-3,4-dihydro-2H-1,2,4-benzothiadiazine-7-sulfonamide), polythiazide (6-chloro-2-methyl-3-{[(2,2,2-trifluoroethyl)thio]methyl}-3,4-dihydro-2H-1,2,4-benzothiadiazine-7-sulfonamide 1,1-dioxide), and hydroflumethiazide (1,1-Dioxo-6-(trifluoromethyl)-3,4-dihydro-2H-1,2,4-benzothiadiazine-7-sulfonamide) are contemplated for reducing SBP.

In other aspects, combination dosages comprising A2-73 and at least one ACE inhibitor, such as enalapril ((2S)-1-[(2S)-2-{[(2S)-1-ethoxy-1-oxo-4-phenylbutan-2-yl]amino}propanoyl]pyrrolidine-2-carboxylic acid), ramipril ((2S,3aS,6aS)-1-[(2S)-2-[[(2S)-1-ethoxy-1-oxo-4-phenylbutan-2-yl]amino]propanoyl]-3,3a,4,5,6,6a-hexahydro-2H-cyclopenta[b]pyrrole-2-carboxylic acid), quinapril ((3S)-2-[(2S)-2-[[(2S)-1-ethoxy-1-oxo-4-phenylbutan-2-yl]amino]propanoyl]-3,4-dihydro-1H-isoquinoline-3-carboxylic acid), perindopril ((2S,3aS,7aS)-1-[(2S)-2-{[(2S)-1-ethoxy-1-oxopentan-2-yl]amino}propanoyl]-octahydro-1H-indole-2-carboxylic acid), lisinopril ((2S)-1-[(2S)-6-amino-2-[[(1S)-1-carboxy-3-phenylpropyl]amino]hexanoyl]pyrrolidine-2-carboxylic acid), benazepril (2-[(3S)-3-[[(2S)-1-ethoxy-1-oxo-4-phenylbutan-2-yl]amino]-2-oxo-4,5-dihydro-3H-1-benzazepin-1-yl]acetic acid), imidapril ((4S)-3-[(2S)-2-[[(2S)-1-ethoxy-1-oxo-4-phenylbutan-2-yl]amino]propanoyl]-1-methyl-2-oxoimidazolidine-4-carboxylic acid), trandolapril ((2S,3aR,7aS)-1-[(2S)-2-{[(2S)-1-ethoxy-1-oxo-4-phenylbutan-2-yl]amino}propanoyl]-octahydro-1H-indole-2-carboxylic acid), cilazapril ((4S,7S)-7-[[(2S)-1-Ethoxy-1-oxo-4-phenylbutan-2-yl]amino]-6-oxo-1,2,3,4,7,8,9,10-octahydropyridazino[1,2-a]diazepine-4-carboxylic acid), fosinopril ((2S,4S)-4-cyclohexyl-1-[2-[hydroxy(4-phenylbutyl)phosphoryl]acetyl]pyrrolidine-2-carboxylic acid), captopril ((2S)-1-[(2S)-2-methyl-3-sulfanylpropanoyl]pyrrolidine-2-carboxylic acid), and zofenopril ((2S,4S)-1-[(2S)-3-benzoylsulfanyl-2-methylpropanoyl]-4-phenylsulfanylpyrrolidine-2-carboxylic acid) are contemplated for reducing SBP.

In other aspects, combination dosages comprising A2-73 and at least one calcium channel blocker, such as amlodipine ((RS)-3-ethyl 5-methyl 2-[(2-aminoethoxy)methyl]-4-(2-chlorophenyl)-6-methyl-1,4-dihydropyridine-3,5-dicarboxylate), clinidipine (3-(E)-3-Phenyl-2-propenyl 5-2-methoxyethyl 2,6-dimethyl-4-(m-nitrophenyl)-1,4-dihydropyridine-3,5-dicarboxylate), clevidipine ((RS)-5-O-(Butanoyloxymethyl) 3-O-methyl 4-(2,3-dichlorophenyl)-2,6-dimethyl-1,4-dihydropyridine-3,5-dicarboxylate), felodipine ((RS)-3-ethyl 5-methyl 4-(2,3-dichlorophenyl)-2,6-dimethyl-1,4-dihydropyridine-3,5-dicarboxylate), isradipine (3-methyl 5-propan-2-yl 4-(2,1,3-benzoxadiazol-4-yl)-2,6-dimethyl-1,4-dihydropyridine-3,5-dicarboxylate), lercanidipine ((RS)-2[(3,3-Diphenylpropyl)(methyl)amino]-1,1-dimethylethyl methyl 2,6-dimethyl-4-(3-nitrophenyl)-1,4-dihydropyridine-3,5-dicarboxylate), levamlodipine ((S)-3-ethyl 5-methyl 2-[(2-aminoethoxy)methyl]-4-(2-chlorophenyl)-6-methyl-1,4-dihydropyridine-3,5-dicarboxylate), nicardipine (2-[benzyl(methyl)amino]ethylmethyl-2,6-dimethyl-4-(3-nitrophenyl)-1,4-dihydropyridine-3,5-dicarboxylate), nifedipine (3,5- dimethyl 2,6-dimethyl-4-(2-nitrophenyl)-1,4-dihydropyridine-3,5-dicarboxylate), nimodipine (3-(2-methoxyethyl) 5-propan-2-yl 2,6-dimethyl-4-(3-nitrophenyl)-1,4-dihydropyridine-3,5-dicarboxylate), nisoldipine (isobutyl methyl 2,6-dimethyl-4-(2-nitrophenyl)-1,4-dihydropyridine-3,5-dicarboxylate), nitrendipine ((RS)-3-Ethyl 5-methyl 2,6-dimethyl-4-(m-nitrophenyl)-1,4-dihydropyridine-3,5-dicarboxylate), diltiazem (cis-(+)-[2-(2-Dimethylaminoethyl)-5-(4-methoxyphenyl)-3-oxo-6-thia-2-azabicyclo[5.4.0]undeca-7,9,11-trien-4-yl]ethanoate), and verapamil ((RS)-2-(3,4-Dimethoxyphenyl)-5-{[2-(3,4-dimethoxyphenyl)ethyl]-(methyl)amino}-2-prop-2-ylpentanenitrile) are contemplated for reducing SBP.

In related aspects, contemplated dosage regimens include administering to the subject a pharmaceutical composition comprising A2-73 on at least a daily basis. Twice daily administration is also expressly contemplated, and a daily dosage as described herein may be split into two equal doses. Administration may continue once daily, or twice daily, for a period of at least 2, 4, 5, 6, 7, 8, 9, 10, 11, 12, 13, 14, 15, 16, 17, 18, 19, 20, 21, 22, 23, 24, 25, 26, 27, 28, 29 or 30 days, or indefinitely for more than 30 days, for 2, 3, 4, 5, 6, 7, 8, 9, 10, 11 or 12 months, or longer. In other aspects, A2-73 is administered according to an intermittent dosing regimen of at least one or two cycles, each cycle comprising (a) a dosing period during which a therapeutically effective dose of said pharmaceutical composition is administered to said patient and, thereafter, (b) a resting period. In some aspects the dosing period and the resting period are of the same duration, or are of different durations. In some aspects the administration is at least daily during the dosing period.

In some aspects, the dosing period and the resting period are in the range of a lower limit of about 1 day, 2 days, 3 days, 4 days, 5 days, 6 days, 7 days, 8 days, 9 days, 10 days, 11 days, 12 days, 13 days, and 14 days to an upper limit of about 28 days, 27 days, 26 days, 25 days, 24 days, 23 days, 22 days, 21 days, 20 days, 19, days, 18 days, 17 days, 16 days, 15 days, and 14 days. It should be understood from the foregoing that various combinations of dosing period length and resting period length are contemplated, and can be adapted as needed to the responsiveness of the patient. As one simple example, a dosing period and alternating resting period regimen may each be 1 day, as follows: $1^{st}$ day, $1^{st}$ dose/$2^{nd}$ day rest/$3^{rd}$ day, $2^{nd}$ dose/$4^{th}$ day rest, and so on. Also noted is a dosing period of between about 1 day and 12 days alternating with a resting period between about 1 day and 12 days, in any combination, with particular reference to a dosing period of 12 days and a resting period of 12 days. An intermittent dosing regimen is usefully employed wherein the therapeutically effective amount of said pharmaceutical composition of A2-73 is about 1 mg to about 60 mg and particularly about 30 mg to about 50 mg, particularly for oral dosage forms. Also contemplated are A2-73 dosages of about 3 mg to about 5 mg particularly with intravenous administration.

It should be understood that the doses, and dosage schedule can be varied according to the characteristics and responsiveness of the subject. Blood pressure can be readily monitored using any method known in the art.

All numbers and ranges disclosed herein may vary by some amount. Whenever a numerical range with a lower limit and an upper limit is disclosed, any number and any included range falling within the range is specifically disclosed. In particular, every range of values (of the form, "from about a, to about b" or equivalently, "from approximately a to b," or, equivalently, "from approximately a-b") disclosed herein is to be understood to set forth every number and range encompassed within the broader range of values.

The compositions disclosed herein individually or in combination are employed in admixture with conventional excipients, i.e., pharmaceutically acceptable organic or inorganic carrier substances suitable for parenteral, enteral (e.g., oral or inhalation) or topical application which do not deleteriously react with the active compositions. Suitable pharmaceutically acceptable carriers include but are not limited to water, salt solutions, alcohols, gum arabic, vegetable oils, benzyl alcohols, polyethylene glycols, gelatin, carbohydrates such as lactose, amylose or starch, magnesium stearate, talc, titanium dioxide, silicic acid, viscous paraffin, perfume oil, fatty acid esters, hydroxyl methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with active compositions. They can also be combined where desired with other active agents, e.g., vitamins.

In some aspects, dosage forms include instructions for the use of such compositions. For parenteral application, particularly are injectable, sterile solutions, preferably oily or aqueous solutions, as well as suspensions, emulsions, or implants, including suppositories. Ampules, vials, and injector cartridges are convenient unit dosages. "Unit dosage form" shall mean single administration entity. By way of example, a single tablet, capsule, dragee, or trochee, suppository, or syringe.

Also for enteral application, particularly suitable are tablets, dragees, liquids, drops, suppositories, or capsules. Syrup, elixir, or the like can be used wherein a sweetened vehicle is employed. Sublingual and buccal forms are also noted.

Sustained or direct release compositions can be formulated, e.g., liposomes or those wherein the active component is protected with differentially degradable coatings, e.g., by microencapsulation, multiple coatings, etc. It is also possible to freeze-dry the new compositions and use the lyophilizates obtained, for example, for the preparation of products for injection.

EXAMPLES

The following examples show uses of A2-73 in the treatment of patients with high SBP. The Examples are illustrative of the invention and are not intended to limit the scope of the invention as described in detail above and as set forth in the claims.

Example 1

Effect of 5 mg and 30 mg Once Daily dosage A2-73.

A 70 year old male that has been taking 5 mg A2-73 orally once a day exhibits a 24-hour ambulatory systolic blood pressure of 150 mg Hg. The dose of A2-73 is then increased so that the subject is administered A2-73 daily, at a dosage of 30 mg/day for a period of 25 days. His 24-hour ambulatory systolic blood pressure is then measured at 135 mg Hg and maintained indefinitely with the daily oral dose of 30 mg of A2-73.

Example 2

Effect of 50 mg Once Daily Dosage A2-73 Combination Treatment with a $\beta_1$-Selective Agent.

A 75 year old female that has been taking metoprolol tartrate 50 mg twice daily exhibits a 24-hour maximum diurnal systolic blood pressure of 150 mg Hg. The subject continues on the metoprolol tartrate, and is started on oral A2-73 at a daily dosage of 50 mg/day for a period of 25 days. Her maximum diurnal systolic blood pressure is then measured at 135 mg Hg and maintained indefinitely with the combined metoprolol tartrate and daily oral dose of 50 mg of A2-73.

Example 3

Effect of 10 mg Once Daily Dosage A2-73 Combination Treatment with a Thiazine Diuretic.

A 60 year old male that has been taking chlorothalidone 25 mg orally once a day exhibits a trough (as to chlorothalidone) systolic blood pressure of 150 mg Hg. The subject continues on the chlorothalidone and is started on oral A2-73 at a daily dosage of 10 mg/day for a period of 25 days. His trough systolic blood pressure is then measured at 135 mg Hg and maintained indefinitely with the combined chlorothalidone and daily oral dose of 10 mg of A2-73.

What is claimed is:

1. A method of treating isolated systolic hypertension, the method comprising administering to a subject in need thereof a therapeutically effective amount of tetrahydro-N,N-dimethyl-2,2-diphenyl-3-furanmethanamine hydrochloride (A2-73), wherein the therapeutically effective amount of A2-73 is between 1 mg and 60 mg.

2. The method of claim 1, wherein the therapeutically effective amount of A2-73 is between 30 and 50 mg.

3. The method of claim 2, wherein the therapeutically effective amount of tetrahydro-N,N-dimethyl-2,2-diphenyl-3-furanmethanamine hydrochloride (A2-73) is administered orally.

4. The method of claim 1, wherein the therapeutically effective amount of A2-73 is between 3 and 5 mg.

5. The method of claim 4, wherein the therapeutically effective amount of A2-73 is administered intravenously.

6. A method for lowering isolated systolic blood pressure in a subject in need thereof, the method comprising administering to the subject tetrahydro-N,N-dimethyl-2,2-diphenyl-3-furanmethanamine hydrochloride (A2-73) at a dose and frequency effective to provide a reduction of at least about 3 mmHg in one or more blood pressure parameters selected from trough sitting systolic, 24-hour ambulatory systolic, and maximum diurnal systolic blood pressures; wherein the subject exhibits resistance to antihypertensive therapy with one or more antihypertensive drugs that are not A2-73.

7. A method for lowering isolated systolic blood pressure in a subject in need thereof, the method comprising administering to the subject tetrahydro-N,N-dimethyl-2,2-diphenyl-3-furanmethanamine hydrochloride (A2-73) in combination with an antihypertensive drug at a dose and frequency effective to provide a reduction of at least about 3 mmHg in one or more blood pressure parameters selected from trough sitting systolic, 24-hour ambulatory systolic, and maximum diurnal systolic blood pressures.

8. The method of claim 6, wherein the antihypertensive drug is selected from the group consisting of beta blockers, thiazide diuretics, ACE inhibitors, and calcium channel blockers.

9. The method of claim 8, wherein the beta blocker is selected from the group comprising propanolol, burcindolol, carteolol, carvedilol, labetalol, nadolol, oxprenolol, penbutolol, pindolol, sotalol, timolol, acebutolol, atenolol, betaxolol, bisoprolol, celiprolol, metoprolol, nebivolol, esmolol, ICI-118,551, and SR 59230A.

10. The method of claim 8, wherein the thiazine diuretic is selected from the group consisting of chlorthalidone, hydrochlorothiazide, methyclothiazide, metolazone, indapamide, bendroflumethiazide, polythiazide, and hydroflumethiazide.

11. The method of claim 8, wherein the ACE inhibitor is selected from the group consisting of enalapril, ramipril, quinapril, perindopril, lisinopril, benazepril, imidapril, trandolapril, cilazapril, fosinopril, captopril, and zofenopril.

12. The method of claim 8, wherein the calcium channel blocker is selected from the group consisting of amlodipine, clinidipine, clevidipine, felodipine, isradipine, lercanidipine, levamlodipine, nicardipine, nifedipine, nimodipine, nisoldipine, nitrendipine, diltiazem, and verapamil.

13. The method of claim 6, wherein the dose of A2-73 is administered to the subject at least once daily.

14. The method of claim 6, wherein the dose of A2-73 is administered to the subject twice daily.

15. The method of claim 14, wherein the twice daily dose of A2-73 is split into two equal doses.

16. The method of claim 6, wherein the dose of A2-73 is administered according to an intermittent dosing regimen of at least two cycles, each cycle comprising a dosing period and a resting period.

17. The method of claim 16, wherein the dosing period and the resting period are of the same duration.

18. The method of claim 16, wherein the dosing period and the resting period are of different durations.

19. The method of claim 16, wherein the dosing period and the resting period are each of a duration selected from the range of 1-28 days.

20. The method of claim 16, wherein the dose of A2-73 is 30-50 mg administered to the subject daily for a period of 14 to 28 days, wherein the subject exhibits a systolic blood pressure of no more than 135 mg Hg.

21. The method of claim 16, wherein the subject is maintained on the daily oral dose of A2-73.

22. The method of claim 7, wherein the subject is maintained on a once daily oral dose of the A2-73 and the antihypertensive drug.

* * * * *